United States Patent
Riu et al.

(10) Patent No.: US 10,351,875 B2
(45) Date of Patent: Jul. 16, 2019

(54) **METHOD FOR PRODUCING TRANSGENIC PLANT WITH INCREASED CONTENT OF 20-HYDROXYECDYSONE USING CYP85 GENE FROM *SPINACIA OLERACEA* AND THE PLANT THEREOF**

(71) Applicant: WOOJUNG BIO INC., Gyeonggi-do (KR)

(72) Inventors: Key Zung Riu, Jeju-do (KR); Kyung Hwan Boo, Jeju-do (KR); Jong Cheol Ahn, Gyeonggi-do (KR)

(73) Assignee: WOOJUNG BIO INC., Gyeonggi-Do (KR)

( * ) Notice: Subject to any disclaimer, the term of this patent is extended or adjusted under 35 U.S.C. 154(b) by 348 days.

(21) Appl. No.: 15/100,379

(22) PCT Filed: Nov. 27, 2014

(86) PCT No.: PCT/KR2014/011496
§ 371 (c)(1),
(2) Date: May 31, 2016

(87) PCT Pub. No.: WO2015/080494
PCT Pub. Date: Jun. 4, 2015

(65) Prior Publication Data
US 2016/0304899 A1    Oct. 20, 2016

(30) Foreign Application Priority Data

Nov. 28, 2013  (KR) .................. 10-2013-0146068

(51) Int. Cl.
*C12N 15/82* (2006.01)
*C12N 9/02* (2006.01)

(52) U.S. Cl.
CPC ....... *C12N 15/8286* (2013.01); *C12N 9/0071* (2013.01); *C12N 15/8241* (2013.01); *C12N 15/8243* (2013.01); *C12Y 114/00* (2013.01); *Y02A 40/162* (2018.01)

(58) Field of Classification Search
None
See application file for complete search history.

(56) References Cited

U.S. PATENT DOCUMENTS

| 4,940,838 A | 7/1990 | Schilperoort et al. |
| 2009/0300785 A1* | 12/2009 | Baerends ................. A01H 5/12 800/268 |
| 2013/0042366 A1 | 2/2013 | Mankin et al. |

FOREIGN PATENT DOCUMENTS

| EP | 0116718 B1 | 5/1990 |
| EP | 0120516 B1 | 10/1991 |
| EP | 0301316 B1 | 6/1993 |
| KR | 10-2007-0044681 A | 4/2007 |
| KR | 10-0795365 B1 | 1/2008 |
| KR | 100834380 B1 | 6/2008 |
| KR | 10-2012-0036711 A | 4/2012 |
| KR | 101256277 B1 | 4/2013 |
| WO | 2012-159196 A1 | 11/2012 |

OTHER PUBLICATIONS

Fang-Meng, Duan, PhD Thesis, JEJU National University, Jun. 2011.*
Festucci-Buselli et al, Botany (2008) 86:978-987.*
Tarkowska et al, Planta (2016) 244:545-555.*
Schmelz et al, Archives of Insect Biochem. and Physiol. (2002) 51:204-221.*
Tanaka et al, Plant Cell Reports (1993) 13:87-90.*
GenBank Accession No. FX897050.1, submitted on Nov. 4, 2014.*
Duan, Fang-Meng, Effect of Phytoecdysteroids on Insect and Construct ion of Biological System for Analyzing of Phytoecdysteroids Biosynthesis, A Thesis for the Degree of Doctor of Philosophy at Jeju National University, p. 1-p. 125 Jun. 2011. See pp. 1, 41, 42, 53, 56, 79, 95, 101, 104 and 109; figures 11, 15, 42 and 49.
Negrutiu I. et al., Hybrid genes in the analysis of transformation conditions, Plant Mol. Biol. 8, p. 363-p. 373, Jun. 1987.
Krens, F.A. et al., In vitro transformation of plant protoplasts with Ti-plasmid DNA, Nature 296, p. 72-p. 74, Mar. 4, 1982.
Shillito R.D. et al., High Efficiency Direct Gene Transfer to Plants, Bio/Technol. 3, p. 1099-p. 1102, Dec. 1985.
Crossway A. et al., Integration of foreign DNA following microinjection of tobacco mesophyll protoplasts, Mol. Gen. Genet. 202, p.179-p. 185, 1986.
Klein T.M. et al., High-velocity microprojectiles for delivering nucleic acids into living cells, Nature 327, p. 70, May 7, 1987.
Handbook of Plant Cell Culture, vol. 1-5, 1983-1989 Momillan, N.Y.

* cited by examiner

*Primary Examiner* — Mykola V. Kovalenko
(74) *Attorney, Agent, or Firm* — The PL Law Group, PLLC

(57) ABSTRACT

A method for producing a transgenic plant which has increased content of 20-hydroxyecdysone compared to a wild type plant includes transforming a plant cell with a recombinant vector containing a gene encoding CYP85 (cytochrome P450, 85 family) protein derived from spinach (*Spinacia oleracea*). A method for producing a transgenic plant with enhanced insect resistance includes transformation of a plant cell with a recombinant vector containing a gene encoding CYP85 derived from *Spinacia oleracea*.

4 Claims, 5 Drawing Sheets

Specification includes a Sequence Listing.

METHOD FOR PRODUCING TRANSGENIC PLANT WITH INCREASED CONTENT OF 20-HYDROXYECDYSONE USING CYP85 GENE FROM *SPINACIA OLERACEA* AND THE PLANT THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2014/011496, filed Nov. 27, 2014, which claims priority to the benefit of Korean Patent Application No. 10-2013-0146068 filed in the Korean Intellectual Property Office on Nov. 28, 2013, the entire contents of which are incorporated herein by reference.

The present invention relates to a method for producing a transgenic plant with increased content of 20-hydroxyecdysone using CYP85 gene from spinach (*Spinacia oleracea*) and a plant produced by the production method. More specifically, the present invention relates to a method for producing a transgenic plant which has increased content of 20-hydroxyecdysone compared to a wild type plant according to transformation of a plant cell with a recombinant vector containing a gene encoding CYP85 (cytochrome P450, 85 family) protein derived from *Spinacia oleracea*, a transgenic plant with increased content of 20-hydroxyecdysone compared to a wild type plant which is produced by the above method and a seed thereof, a composition for increasing content of 20-hydroxyecdysone in plant which contains a gene encoding CYP85 protein derived from *Spinacia oleracea* as an effective component, a method for producing a transgenic plant with enhanced insect resistance according to transformation of a plant cell with a recombinant vector containing a gene encoding CYP85 derived from *Spinacia oleracea*, a transgenic plant with enhanced insect resistance which is produced by the above method and a seed thereof, and a composition for enhancing insect resistance of a plant which contains a gene encoding CYP85 protein derived from *Spinacia oleracea* as an effective component.

BACKGROUND ART

Ecdysteroids are a steroid hormone responsible for the regulation of molting of an insect, and it has been first discovered by Butenanadt and Karlson in 1954. After that, in 1996, ecdysteroids were firstly identified in plant by NaKanishi and Koreeda. Ecdysteroids are one group of 2,3,14-trihydroxy-Δ-7-ketosteroids, and they are the compound belonging to polyhydroxylated steroids including known ecdysterons and ecdysones or the like. Although their activity in plant is not fully known, plant ecdysteroids are known to exhibit an influence on a plant defense mechanism as they show an effect of inhibiting feeding, avoidance, and insecticidal activity against some non-adapted phytophagous insects.

Meanwhile, cytochrome P450 (CYP) is contained in various plants, and as an enzyme having heme structure, it is found not only in a plant but also in microbes, molds, and mammals. In particular, many family types of cytochrome P450 gene are found in several plants in which it constitutes almost 1% of the whole genome. Also in *Arabidopsis thaliana*, 246 cytochrome P450 genes and 26 pseudo cytochrome P450 are identified and reported. In plant, they are known to be involved with a biosynthetic reaction of a plant hormone or play a role of a signal transducing molecule or an element of a defensive reaction. It is also known to be involved with a biosynthetic pathway of a natural plant material like phenylpropanoids, alkaloids, terpenoids, lipids, cyanogenic glycosides, and glucosinolates as well as auxins, gibberellins, jasmonic acid, and brassinosteroids that are known as a plant growth regulator. In particular, cytochrome P450 exhibits an enhanced expression in response to a stimulation form outside like attacks by molds, microbes, insects, or mammals, and the enhanced expression leads to synthesis of materials that are related to a defensive reaction of a plant. Based on these facts, it is expected that cytochrome P450 can be used, together with a study and understanding of related genes and a signal transduction system, for development of a bioengineered plant with increased resistance to harmful insects or, as a plant genetic material having resistance to harmful insects, it can be practically used for molecular breeding or the like.

Meanwhile, in Korean Patent Registration No. 0834380, "Cytochrome P450 gene for enhancing water resistance of plant by using CYP78A7 derived from *Arabidopsis thaliana*" is disclosed, and in Korean Patent Registration No. 1256277, "Cytochrome P450 gene (CaCYP450A) from pepper which is involved with resistance reaction against pathogen and disease-resistant transgenic plant using the same" is disclosed. However, there is no description related to the method for producing a transgenic plant with increased content of 20-hydroxyecdysone using CYP85 gene from *Spinacia oleracea* and a plant produced by the production method as described in the present invention.

SUMMARY

The present invention is devised in view of the above-described needs, and according to the present invention, a transgenic plant in which the gene encoding CYP85 derived from *Spinacia oleracea* is over-expressed is produced. Further, by confirming that the content of 20-hydroxyecdysone is increased in the transgenic plant compared to a non-transgenic plant, the present invention is completed accordingly.

In order to solve the problems described above, the present invention provides a method for producing a transgenic plant with increased content of 20-hydroxyecdysone compared to a wild type plant comprising:

transforming a plant cell with a recombinant vector containing a gene encoding CYP85 (cytochrome P450, 85 family) protein derived from spinach (*Spinacia oleracea*); and, regenerating a plant from the above transformed plant cell.

The present invention further provides a transgenic plant with increased content of 20-hydroxyecdysone compared to a wild type plant which is produced by the above method, and a seed thereof.

The present invention further provides a composition for increasing content of 20-hydroxyecdysone in plant which contains a gene encoding CYP85 protein derived from *Spinacia oleracea* as an effective component.

The present invention further provides a method for increasing content of 20-hydroxyecdysone in plant compared to a wild type plant comprising transforming a plant cell with a recombinant vector containing a gene encoding CYP85 (cytochrome P450, 85 family) protein derived from spinach (*Spinacia oleracea*) and over-expressing the CYP85 gene.

The present invention further provides a method for producing a transgenic plant with increased insect resistance comprising:

transforming a plant cell with a recombinant vector containing a gene encoding CYP85 (cytochrome P450, 85 family) protein derived from spinach (*Spinacia oleracea*); and, regenerating a plant from the above transformed plant cell.

The present invention further provides a transgenic plant with enhanced insect resistance which is produced by the above method, and a seed thereof.

The present still further provides a composition for enhancing insect resistance of a plant which contains a gene encoding CYP85 protein derived from *Spinacia oleracea* as an effective component.

According to the present invention, it was confirmed that content of 20-hydroxyecdysone is increased in plant when the gene encoding CYP85 protein derived from *Spinacia oleracea* is over-expressed. Because 20-hydroxyecdysone exhibits an influence on a plant defense mechanism as it shows an effect of inhibiting feeding, avoidance, and insecticidal activity against some harmful insects, an agricultural product with enhanced insect resistance can be produced by using the gene encoding CYP85 protein derived from *Spinacia oleracea* of the present invention, and a composition for controlling harmful insects can be developed by using increased 20-hydroxyecdysone. As such, it is believed to have an industrial usefulness.

DETAILED DESCRIPTION

Figure 1:
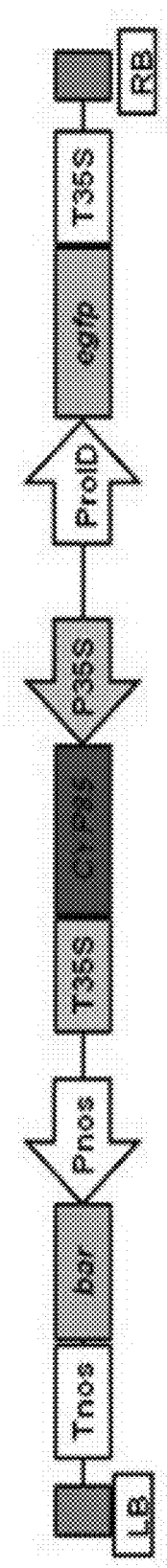
FIG. 1 is a schematic diagram illustrating the recombinant vector pB7WG2D,1 which includes the gene encoding CYP85 protein derived from *Spinacia oleracea* of the present invention.

In order to achieve the object of the present invention, the present invention provides a method for producing a transgenic plant with increased content of 20-hydroxyecdysone compared to a wild type plant comprising:

transforming a plant cell with a recombinant vector containing a gene encoding CYP85 (cytochrome P450, 85 family) protein derived from spinach (*Spinacia oleracea*); and, regenerating a plant from the above transformed plant cell.

Included in the scope of the CYP85 protein of the present invention are the protein having an amino acid sequence represented by SEQ ID NO: 2 and functional equivalents of the protein. As described herein, the expression "functional equivalents" means a protein which has, as a result of addition, substitution, or deletion of an amino acid, at least 70%, preferably at least 80%, more preferably at least 90%, and even more preferably at least 95% sequence homology with the amino acid sequence represented by SEQ ID NO: 2, and it indicates a protein which exhibits substantially the same physiological activity as the protein represented by SEQ ID NO: 2. The expression "substantially the same physiological activity" indicates an activity of controlling the content of 20-hydroxyecdysone in a plant.

The present invention also provides a gene encoding the CYP85 protein. The gene of the present invention may contain the nucleotide sequence of SEQ ID NO: 1. Further, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence of SEQ ID NO: 1. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the CYP85 gene sequence may be inserted to the recombinant expression vector. The expression "recombinant expression vector" means a bacteria plasmid, a phage, a yeast plasmid, a plant cell virus, a mammalian cell virus, or other vector. In general, as long as it can be replicated and stabilized in a host, any plasmid or vector can be used. Important characteristic of the expression vector is that it has a replication origin, a promoter, a marker gene, and a translation control element.

The expression vector comprising the CYP85 gene sequence and a suitable signal for regulating transcription/translation can be constructed by a method which is well known to a person in the art. Examples of such method include an in vitro recombination DNA technique, a DNA synthesis technique, and an in vivo recombination technique. The DNA sequence can be effectively linked to a suitable promoter in the expression vector in order to induce synthesis of mRNA. Furthermore, the expression vector may contain, as a site for translation initiation, a ribosome binding site and a transcription terminator.

A preferred example of the recombinant vector of the present invention is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a genome of a plant. Especially preferred form of Ti-plasmid vector is a so-called binary vector which has been disclosed in EP 0 120 516 B1 and U.S. Pat. No. 4,940,838. Other vector that can be used for introducing the gene of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be advantageous especially when a plant host cannot be easily transformed.

Expression vector would comprise at least one selective marker. Said selective marker is a nucleotide sequence having a property based on that it can be selected by a common chemical method. Every gene which can be used for the differentiation of transformed cells from non-transformed cell can be a selective marker. Example includes, a gene resistant to herbicide such as glyphosate and phosphintricin, and a gene resistant to antibiotics such as kanamycin, G418, bleomycin, hygromycin, and chloramphenicol, but not limited thereto.

For the recombinant vector of the present invention, a promoter can be any of CaMV 35S, actin, ubiquitin, pEMU, MAS or histone promoter, but not limited thereto. The term "promoter" means a DNA molecule to which RNA polymerase binds in order to initiate its transcription, and it corresponds to a DNA region upstream of a structural gene. The term "plant promoter" indicates a promoter which can initiate transcription in a plant cell. The term "constitutive promoter" indicates a promoter which is active in most of environmental conditions and development states or cell differentiation states. Since a transformant can be selected with various mechanisms at various stages, a constitutive promoter can be preferable for the present invention. Therefore, a possibility for choosing a constitutive promoter is not limited herein.

For the recombinant vector of the present invention, any conventional terminator can be used. Examples thereof include nopaline synthase (NOS), rice α-amylase RAmy1 A terminator, phaseoline terminator, and a terminator for optopine gene of *Agrobacterium tumefaciens*, etc., but are not limited thereto. Regarding the necessity of terminator, it is generally known that such region can increase a reliability and an efficiency of transcription in plant cells. Therefore, the use of terminator is highly preferable in view of the contexts of the present invention.

Plant transformation means any method by which DNA is delivered to a plant. Such transformation method does not necessarily need a period for regeneration and/or tissue culture. Transformation of plant species is now quite common not only for dicot plants but also for monocot plants. In principle, any transformation method can be used for introducing a hybrid DNA of the present invention to appropriate progenitor cells. The method can be appropriately selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method for plant components (Crossway A. et al., 1986, Mol. Gen. Genet. 202, 179-185), a particle bombardment method for various plant components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. A method preferred in the present invention includes *Agrobacterium* mediated DNA transfer. In particular, so-called binary vector technique as disclosed in EP A 120 516 and U.S. Pat. No. 4,940,838 can be preferably adopted for the present invention.

The method of the present invention comprises transforming a plant cell with the recombinant vector of the present invention, and the transformation may be mediated by *Agrobacterium tumefaciens*, for example. Further, the method of the present invention comprises regenerating a transgenic plant from the transgenic plant cell. As for the method for regenerating a transgenic plant from a transgenic plant cell, a method well known in the pertinent art can be used.

The transgenic plant cell needs to be regenerated into a whole plant. Techniques for regeneration into a mature plant by culture of callus or protoplast are well known in the pertinent art for various species (Handbook of Plant Cell Culture, Vol. 1-5, 1983-1989 Momillan, N.Y.).

The present invention also provides a transgenic plant with increased content of 20-hydroxyecdysone compared to a wild type plant which is produced by the above method, and a seed thereof.

According to one embodiment of the present invention, the plant can be preferably a dicot plant such as *Arabidopsis thaliana*, potato, eggplant, tobacco, pepper, tomato, burdock, crown daisy, lettuce, balloon flower, spinach, chard, yam, celery, carrot, water parsley, parsley, Chinese cabbage, cabbage, *Raphanus sativus* for. *raphnistroides* MAK, watermelon, oriental melon, cucumber, zucchini, gourd, strawberry, soybean, mung bean, kidney bean, or sweet pea or a monocot plant such as rice, barley, wheat, rye, corn, sugar cane, oat, or onion. Preferably, it is a dicot plant. More preferably, it is a plant of Chenopodiaceae such as gemleini, *Atriplex hastata* L, *Atriplex subcordata* Kitag, chard, sugar beet, *Suaeda glauca* (Bunge) Bunge, *Suaeda australis* (R. Br.) Moq., *Suaeda japonica*, *Suaeda maritima*. (L)., *Kochia scoparia*, Clammy Goosefoot, Maple-leaved Goosefoot, *Chenopodium ambrosioides* L, *Chenopodium ficifolium*, *Atriplex triangularis* Willd, Oakleaf Goosefoot, White Goosefoot, *Salsola komarovii*, *Spinacia oleracea*, *Salicornia europaea*, or *Corispermum platypterum* Kitag. Most preferably, it can be *Spinacia oleracea*, but it is not limited thereto.

The present invention also provides a composition for increasing content of 20-hydroxyecdysone in a plant which contains a gene encoding CYP85 protein as an effective component. The composition contains a gene encoding CYP85 protein which consists of the amino acid sequence of SEQ ID NO: 2 as an effective component, and when a plant is transformed with this gene, content of 20-hydroxyecdysone in the plant can be increased.

The present invention also provides a method for increasing content of 20-hydroxyecdysone in plant compared to a wild type plant comprising transforming a plant cell with a recombinant vector containing a gene encoding CYP85 (cytochrome P450, 85 family) protein derived from spinach (*Spinacia oleracea*) and over-expressing the CYP85 gene.

The present invention also provides a method for producing a transgenic plant with increased insect resistance comprising:

transforming a plant cell with a recombinant vector containing a gene encoding CYP85 (cytochrome P450, 85 family) protein derived from spinach (*Spinacia oleracea*); and regenerating a plant from the above transformed plant cell.

As described herein, the expression "insect resistance" includes the resistance and tolerance which is exhibited by a plant against harmful insects, and it includes inhibited preference of harmful insect for host plant, inhibited growth activity of a host against harmful insect, and tolerance not allowing any influence by harmful insects based on strong compensation property or recovery property.

A plant transformed with the recombinant vector which contains a gene encoding CYP85 protein derived from *Spinacia oleracea* of the present invention exhibits increased content of 20-hydroxyecdysone, and 20-hydroxyecdysone is known to exhibit the activity of inhibiting feeding, avoidance, and insecticidal activity against some harmful insects. Accordingly, a plant transformed with the recombinant vector which contains a gene encoding CYP85 protein derived from *Spinacia oleracea* may exhibit enhanced insect resistance due to the increased 20-hydroxyecdysone.

The present invention also provides a transgenic plant with enhanced insect resistance which is produced by the above method, and a seed thereof.

The plant of the present invention is as defined in the above.

The present also provides a composition for enhancing insect resistance of a plant which contains a gene encoding CYP85 protein derived from *Spinacia oleracea* as an effective component. The composition of the present invention contains a gene encoding CYP85 protein which consists of the amino acid sequence of SEQ ID NO: 2 as an effective component, and as a plant is transformed with this gene encoding CYP85 protein to express the protein, insect resistance of the plant can be enhanced.

Hereinbelow, the present invention is explained in greater detail in view of the Examples. However, it is evident that the following Examples are given only for exemplification of the present invention and by no means the present invention is limited to the following Examples.

Example 1. Cloning of *Spinacia oleracea* CYP85 Gene and Construction of Plant Expression Vector A gene encoding CYP85 (cytochrome P450, 85 family) protein was cloned from spinach (*Spinacia oleracea*). Cloned CYP85 gene was inserted to plant expression vector pB7WG2D,1 by using gateway system. The vector was designed such that expression of CYP85 gene is controlled by 35S promoter. Furthermore, as a reporter gene, EGFP gene was used, and bar gene was used as a selection marker (FIG. 1).

Example 2. Production of Transgenic Plant

From a root of germ-free *Spinacia oleracea* (winter breed), callus was induced by using ½ MS medium (20 g/l sucrose, 2.5 g/l gellan gum, pH 6.0) added with 5 μM α-naphthalene acetic acid (NAA), 10 μM 6-benzyladenine (BA), and 0.3 μM gibberellic acid (GA3). Induced callus was maintained under sub-culture with an interval of 3 weeks in ½ MS medium (20 g/l sucrose, 2.5 g/l gellan gum, pH 6.0) added with 20 μM NAA, 1 μM BA, and 0.3 μM GA3.

To produce a transgenic plant, 3 to 7 days in advance, the callus was first transferred to ½ MS medium (20 g/l sucrose, 2.5 g/l gellan gum, pH 6.0) added with 20 μM NAA, 5 μM BA, and 0.3 μM GA3. Then, on the day of transformation, the callus was transferred to a filter paper to remove moisture. For transformation, EHA105 *Agrobacterium* cell line was used as a mediator, and for infection of *Agrobacterium* introduced with a target gene, the *Agrobacterium* was suspended to $OD_{300}=0.2$ in MS medium (20 g/l sucrose, 100 μM acetosyringone medium (pH 6.0)) which is free of calcium ion, and a certain amount of the callus was kept in the medium for about 30 minutes. Then, the callus was recovered and dried for 3 to 5 minutes on a filter paper, and subsequently impregnated in a medium containing *Agrobacterium* followed by keeping for 3 to 5 minutes. After that, the callus was recovered, dried on a filter paper for 3 to 5 minutes, and co-cultured for 4 days under dark conditions using MS medium (20 g/l sucrose, 100 μM acetosyringone (pH 5.4)) which is free of calcium ion.

After the co-culture, the callus was impregnated for 30 minutes in ½ MS solution added with 1 mM cefotaxime, dried by using a filter paper, and transferred to ½ MS selection medium (20 g/l sucrose, 2.5 g/l gellan gum, 250 μM cefotaxime, 5 μM phosphinothricin (PPT), pH 6.0) added with 20 μM NAA, 5 μM BA, and 0.3 μM GA3. Then, it was cultured for 4 weeks including 10 hours at 20° C. under light condition and 14 hours at 16° C. under dark condition for first selection of transformed callus. The callus selected from the first selection medium was subjected to the second selection which uses the same medium as above in which PPT concentration is increased by 5 times. 2 to 4 Weeks later, expression of EGFP gene was confirmed and the finally-selected transformed callus was obtained.

Figure 2:
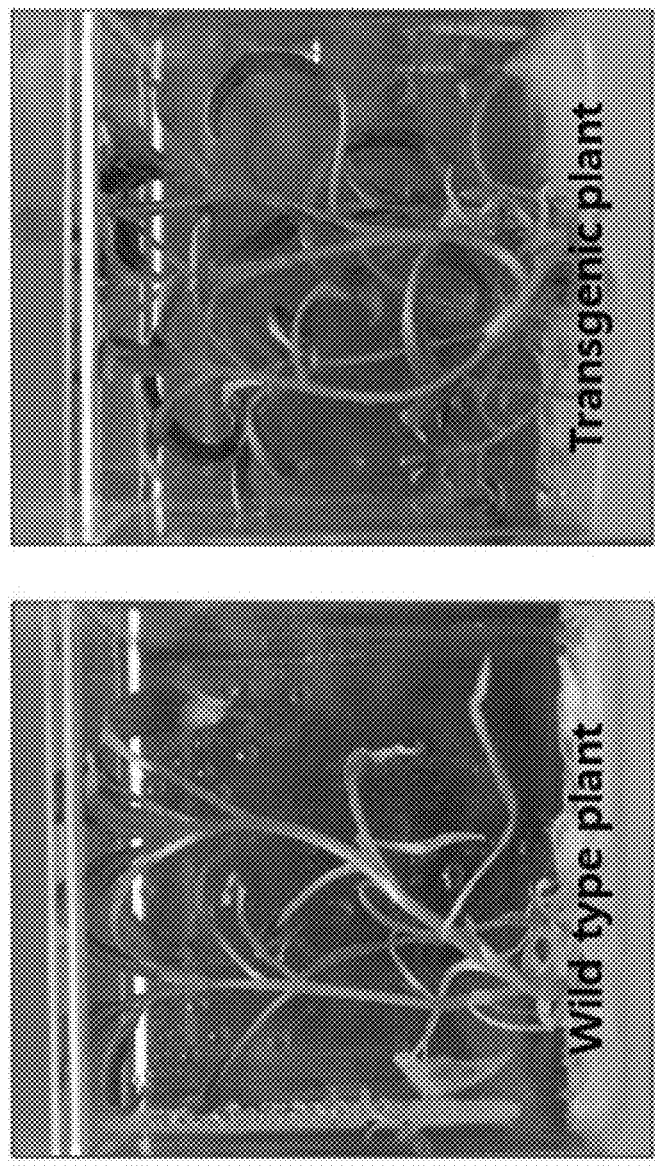
FIG. 2 shows photographic images of *Spinacia oleracea* plants which have been obtained by in vitro tissue culture and transformation, i.e., transgenic plant with over-expressed *Spinacia oleracea* CYP85 gene (right panel: transgenic plant) and wild type control (left panel: wild type plant).

The finally-selected callus was cultured for 4 to 8 weeks in ½ MS medium (20 g/l sucrose, 2.5 g/l gellan gum, 250 μM cefotaxime, pH 6.0) added with 10 μM NAA and 0.3 μM GA3, and the callus exhibiting root formation was selected and transferred to ½ MS medium (20 g/l sucrose, 3 g/l gellan gum, pH 6.0) added with 2 μM NAA and 5 μM BA to induce forming of somatic embryo. From the small plant obtained from somatic embryo, a transgenic plant was selected by determining again the expression of EGFP gene, and after transfer to ½ MS medium (20 g/l sucrose, 8 g/l agar, pH 6.0), it was allowed to grow as a plant (FIG. 2). The *Spinacia oleracea* which has been fully regenerated was transferred to a soil, and after undergoing an acclimation process with maintaining of high humidity for a certain period of time, it was allowed to grow to a mature plant. The control plant was prepared in the same manner as above except the process of *Agrobaterium* infection and selection of transformant.

Example 3. Confirmation of Gene Introduced into Transgenic Plant and Expression Analysis Confirmation of the gene introduced into a transgenic plant was performed by PCR after extracting DNA from a transgenic plant and a control plant, respectively. Total three pairs of primer were used for PCR analysis including a first pair for amplifying a part of a gene introduced with CYP85 gene (soCYP85-F; 5'-GCTGGTATTGAATCAAGCTC-3'; SEQ ID NO: 3, soCYP85-R; 5'-GGTACTTGACAGCCAT-CATT-3'; SEQ ID NO: 4), a second pair for amplifying a region between the 35S promoter site and CYP85 gene site in the recombinant vector used for gene introduction (P35S-

SoCYP85-F; 5'-TTCGCAAGACCCTTCCTCTA-3'; SEQ ID NO: 5, P35S-SoCYP85-R; 5'-CTAATAACTC-GAAACTCGAATGC-3'; SEQ ID NO: 6), and a third pair for amplifying a part of EGFP gene which is used as a reporter gene for gene introduction (EGFP-F; 5'-TCTTTTTCATCTTTTCACTTCTCC-3'; SEQ ID NO: 7, EGFP-R; 5'-TGATATAGACGTTGTGGCTGTTG-3'; SEQ ID NO: 8). In the present invention, introduction of CYP85 gene was confirmed for three kinds of transgenic *Spinacia oleracea* (number: 85201, 850203 and 853282).

Figure 3:
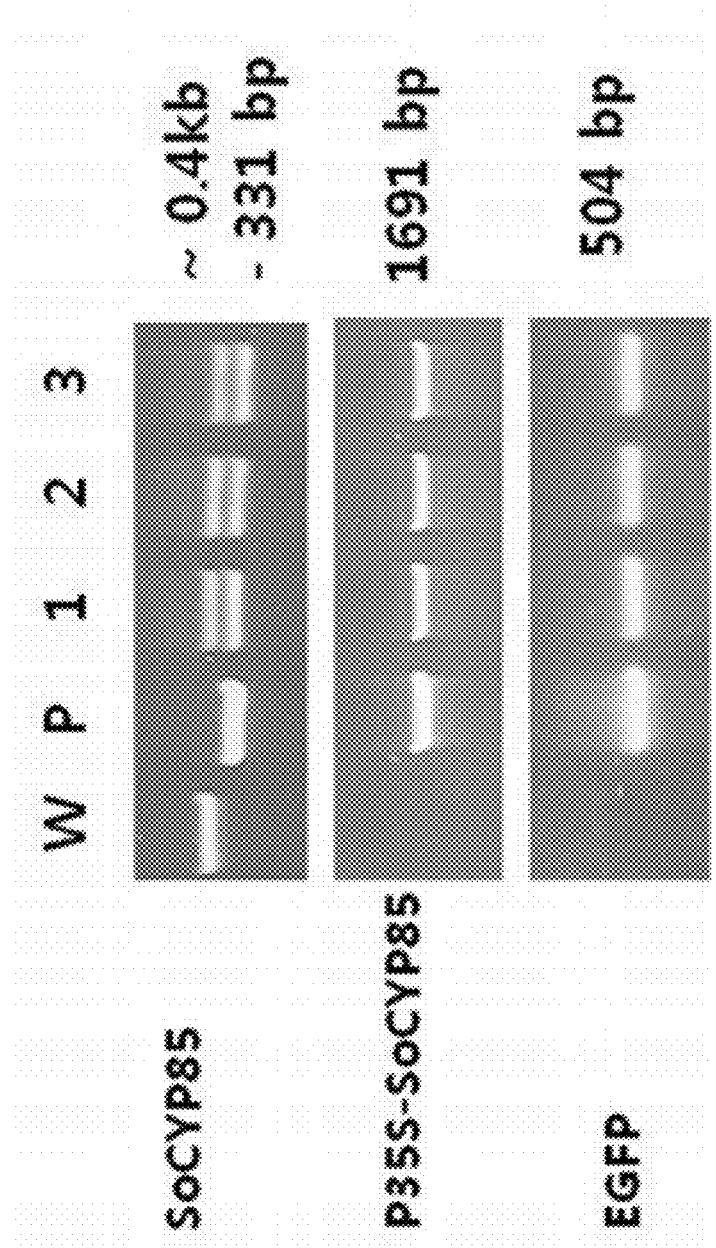
FIG. 3 shows the result of PCR analysis by which incorporation of *Spinacia oleracea* CYP85 gene to a transgenic plant is analyzed by using genomic DNA. SoCYP85, *Spinacia oleracea* CYP85 gene; p35S-SoCYP85, site of promoter and incorporated gene in the recombinant vector; EGFP, reporter gene; W, control group of wild type *Spinacia oleracea*; P, positive control group of plant expression vector containing *Spinacia oleracea* CYP85 gene; 1 to 3, transgenic *Spinacia oleracea*.

As a result, from the non-transgenic control group, the CYP85 gene was detected with one band having 0.4 kb size. However, from the transgenic *Spinacia oleracea*, two bands were shown between 0.3 to 0.4 kb. Based on the result of performing PCR by using the recombinant vector which is used in the present invention as a positive control, it was found that the 0.4 kb band corresponds to CYP85 gene intrinsic to the *Spinacia oleracea*, and 0.3 kb band is an amplification product of the introduced gene (FIG. 3). The difference in gene size is caused by absence of an intron region in the introduced gene, and from the result obtained using the primer (SEQ ID NO: 5 and SEQ ID NO: 6), which is capable of amplifying a region between the 35S promoter used for gene introduction and CYP85 gene, no amplification of the gene is found in the non-transgenic control group. On the other hand, from the transgenic *Spinacia oleracea* and the positive control, an amplified product was found (FIG. 3). Furthermore, according to determination of the introduction, EGFP as a reporter gene was not detected in the non-transgenic control group. On the other hand, the reporter gene was identified from all the transgenic *Spinacia oleracea* plants. The analysis was carried out in the same manner as the above PCR analysis by using three kinds of transgenic *Spinacia oleracea* (number: 85201, 850203 and 853282).

For the transgenic *Spinacia oleracea* from which introduction of CYP85 gene has been confirmed, an increase in expression of the introduced gene was determined at RNA level. Specifically, after extracting the total RNA from the transgenic plant and the control plant, analysis was made by RT-PCR. Total three pairs of primer were used for RT-PCR analysis including a first pair for amplifying a part of CYP85 gene (SEQ ID NO: 3 and SEQ ID NO: 4), a second pair for amplifying a part of EGFP gene which is used as a reporter gene for gene introduction (SEQ ID NO: 7 and SEQ ID NO: 8), and a third pair for amplifying a part of Cyclophilin (CYC), which can be used as a reference for evaluating an increase or a decrease in expression of a target gene (CYC-F; 5'-GATGTTACCCCCAAAACTGCT-3'; SEQ ID NO: 9, CYC-R; 5'-AACAACATGCTTTCCATCCAG-3'; SEQ ID NO: 10).

Figure 4:
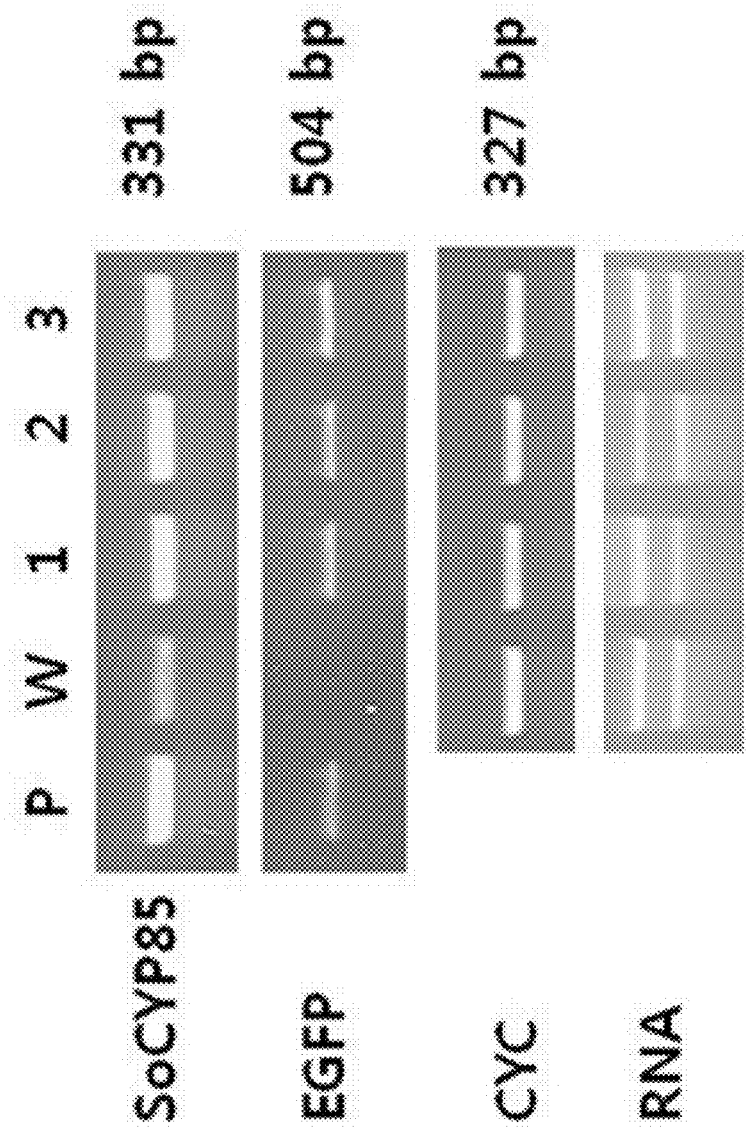
FIG. 4 shows the result of RT-PCR analysis for confirming an increase in expression of *Spinacia oleracea* CYP85 gene in the transgenic plant. SoCYP85, *Spinacia oleracea* CYP85 gene; p35S-SoCYP85, site of promoter and incorporated gene in the recombinant vector; EGFP, reporter gene; W, control group of wild type *Spinacia oleracea*; P, positive control group of plant expression vector containing *Spinacia oleracea* CYP85 gene; 1 to 3, transgenic *Spinacia oleracea*.

As a result, it was found that CYC gene was expressed at the same level in each sample of the three kinds of the transgenic plant and the no-transgenic control group. On the other hand, CYP85 gene expression level was higher in the three kinds of the transgenic *Spinacia oleracea* plant compared to the no-transgenic control. Furthermore, expression of EGFP as a reporter gene was confirmed from all three kinds of the transgenic plant (FIG. 4).

Based on the above result, it was found that all of the three kinds of the transgenic *Spinacia oleracea* plant of the present invention have CYP85 gene introduced therein, and it was also confirmed at DNA level that, compared to the non-transgenic control group, the expression of CYP85 gene is higher in all of the three kinds of the transgenic *Spinacia oleracea* plant having CYP85 gene introduced therein.

Example 4. Analysis of Content of 20-Hydroxyecdysone (20E) in Transgenic Plant

By using the above transgenic plant which has been confirmed to have CYP85 gene introduced therein, a change in content of 20-hydroxyecdysone (20E) was analyzed.

Specifically, for 20E extraction from the non-transgenic control group and the transgenic plant, about 50 mg of dry sample was extracted three times with 5, 2.5, 2.5 ml methanol, and after adding 2.5 ml of water to the extract, phase distribution using 10 ml hexane was performed 2 times. Then, the methanol/water layer was collected, concentrated, and re-dissolved in 500 μM methanol, and the resultant was used as a sample for 20E analysis. For the 20E content analysis, LC/MS/MS was used. Conditions of LC/MS/MS that are used for 20E content analysis of the present invention are as described in the following Table 1.

TABLE 1

| | Conditions |
|---|---|
| Apparatus | Accela pump, Autosampler, PDA detector, LXQ mass spectrophotometry (Thermo Scientific, USA) |
| Conditions | Column: YMC column (250 × 4.6 mm) Solvent: 11% isopropanol in 0.1% TFA in water PDA detector: UV 242 nm Flow rate: 1 ml/minute (0.3 to 0.2 for MS, ~0.8 out) Injection amount: 20 μl Running time: 50 minutes |
| Mass scan | Mass 1 scan range: 100-1000 Mass 2 range: 130-500 Mass 2 parent: 481 |

Figure 5:
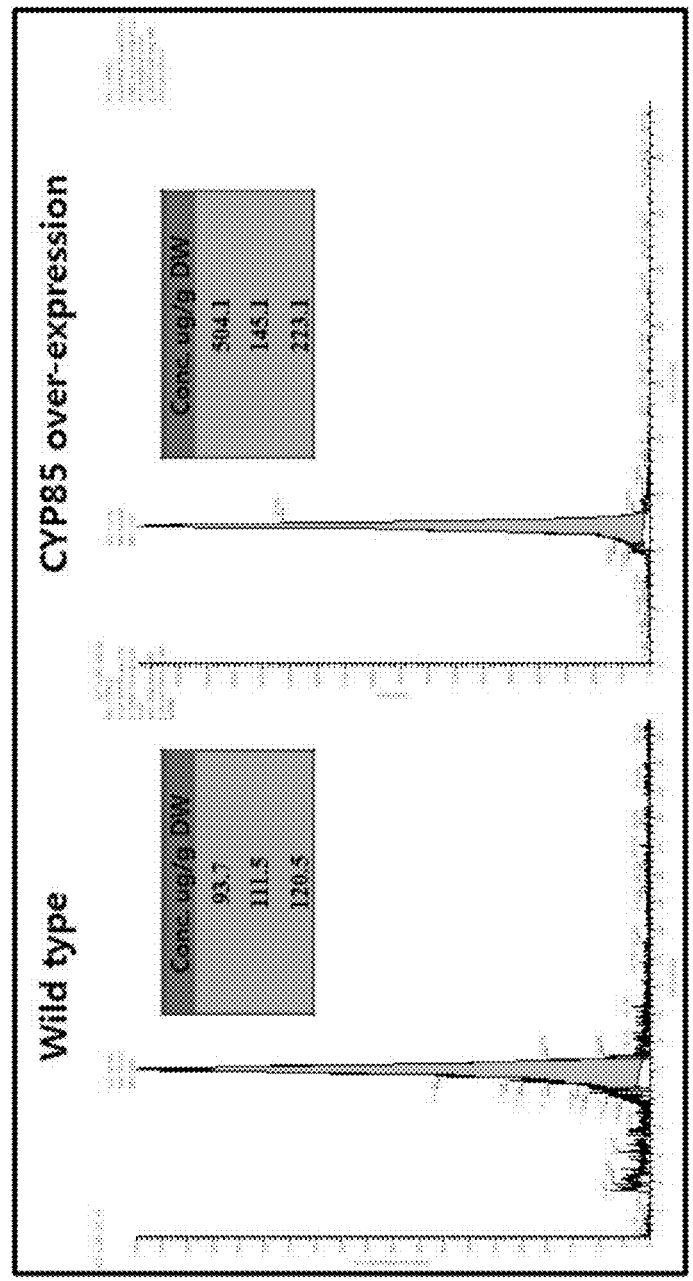
FIG. 5 is a chromatogram illustrating the result of analyzing content of 20-hydroxyecdysone in the wild type *Spinacia oleracea* and the transgenic *Spinacia oleracea* exhibiting over-expression of the CYP85 gene, in which the chromatogram is obtained by LC/MS/MS.

As a result of analyzing the content of 20E, it was found that the average content of 20E is about 100 μg/gram of dry weight in the control plant, but it is about 290 μg/gram of dry weight in the transgenic plant, indicating an increase of about 3 times on average. Among the three types of the transgenic plant, a transgenic plant exhibiting the 20E content increase which is as high as 5 times the control group was also confirmed (FIG. 5).

Based on the above results, it was found that, in the transgenic plant in which CYP85 gene derived from *Spinacia oleracea* is used, content of 20-hydroxyecdysone (i.e., 20E) has clearly increased.

The invention claimed is:

1. A method for producing a transgenic plant with increased content of 20-hydroxyecdysone and increased insect resistance compared to a wild type plant, the method comprising:

transforming a plant cell with a recombinant vector comprising a gene encoding a cytochrome P450, 85 family (CYP85) protein derived from *Spinacia oleracea*, wherein the CYP85 protein consists of SEQ ID NO: 2; and, regenerating a plant from the transformed plant cell, wherein the plant is *Spinacia oleracea*.

2. A transgenic plant with increased content of 20-hydroxyecdysone and increased insect resistance compared to a wild-type plant, wherein the transgenic plant was produced by the method of claim 1, and wherein the transgenic plant comprises the recombinant vector.

3. A seed of the transgenic plant of claim 2, wherein the seed comprises the recombinant vector.

4. A method for increasing content of 20-hydroxyecdysone in a plant compared to a wild type plant, the method comprising transforming a plant cell with a recombinant vector comprising a gene encoding a CYP85 protein derived from *Spinacia oleracea* and, over-expressing the CYP85 gene, wherein the CYP85 protein consists of SEQ ID NO: 2, wherein the plant is *Spinacia oleracea*.

* * * * *

SEQUENCE LISTING

<160> NUMBER OF SEQ ID NOS: 10

<210> SEQ ID NO 1
<211> LENGTH: 1395
<212> TYPE: DNA

<213> ORGANISM: Spinacia oleracea

<400> SEQUENCE: 1

```
atggccgttt ttatggtggt ttttgctgtg attttcagct tgttttgttt ctcttctgct    60
ttgttaagat ggaatgaact tagatatagg aagaaaggat tgccacctgg aactatgggt   120
tggcctatct ttggtgaaac tactgagttc cttaaacaag ctctaacttc attaagaac    180
caaagatcaa gatatgggaa ttttttcaag tcccatatat ggggtgtcc aacaatagtg    240
tcaatggatg cagaactaaa caggttcata ctaatgaatg aatcaaaagg gttagtacca   300
gggtacccac agtctatgtt agacattctt ggaaaatgta acattgctgc tgttcatggc   360
tccactcaca agtacatgag gggtacccct cttcttttgg tcagtcccac catgattaga   420
gatcatattc tccccaaagt tgatcagttt atgagatccc atctctccaa ttggcaaaat   480
catgtcattg acatccaaca aaagactaag gagatggctt cctgtcttc cttaaagcaa    540
attgctggta ttgaatcaag ctcaactgcc caactattta tgtctgaatt cttcaagctt   600
gttgaaggga cactttctct ccctattgac ctccctggca caaattaccg cagggttttt   660
caggcaagga aggtgatagt gaatatattg acacaactta aaagaaag aagagcatca    720
aaaacaaaag atgttgatat tttaaattgt ctattaaaag aagaggagaa caaatataaa   780
ctaagtgatg aagagatcat tgatctcatc attactcttg cttattctgg ttatgaaact   840
gtctcaacta cttcaatgat ggctgtcaag taccttcatg atcaccccca tgttctagaa    900
gagctcagaa agagcatttt ggcaatcaga gcaaaaaaga agccggggga tcctattaac   960
tgggaagatt acaaggctat gaagtttact agagctgtga tatttgagac atcaagatta  1020
gccacaattg ttaatggggt gttgagaaaa acaactaaag agatggaaat aaatggtttc  1080
gtgattccgg aaggttggag aatatatgta tatacaagaa agtaaaatta tgatccgtat  1140
ttgtacccgg atccactcgt cttcaaccca tggagatggc tggataggag cttggaatcg  1200
aagaattatt tcttatatt tggaggtggg acgaggcagt gccctggcaa ggaattagga   1260
attgctgaaa tttctacatt ccttcattat tttgtaacta gatacagatg ggaggaagaa  1320
gagggtaata agctggtaaa gtttcctaga gtggaggcac caaatggatt acgcattcga  1380
gtttcgagtt attag                                                   1395
```

<210> SEQ ID NO 2
<211> LENGTH: 464
<212> TYPE: PRT
<213> ORGANISM: Spinacia oleracea

<400> SEQUENCE: 2

```
Met Ala Val Phe Met Val Val Phe Ala Val Ile Phe Ser Leu Phe Cys
 1               5                  10                  15

Phe Ser Ser Ala Leu Leu Arg Trp Asn Glu Leu Arg Tyr Arg Lys Lys
                20                  25                  30

Gly Leu Pro Pro Gly Thr Met Gly Trp Pro Ile Phe Gly Glu Thr Thr
            35                  40                  45

Glu Phe Leu Lys Gln Gly Ser Asn Phe Ile Lys Asn Gln Arg Ser Arg
        50                  55                  60

Tyr Gly Asn Phe Phe Lys Ser His Ile Leu Gly Cys Pro Thr Ile Val
 65                  70                  75                  80

Ser Met Asp Ala Glu Leu Asn Arg Phe Ile Leu Met Asn Glu Ser Lys
                85                  90                  95

Gly Leu Val Pro Gly Tyr Pro Gln Ser Met Leu Asp Ile Leu Gly Lys
```

|     |     |     |     |     | 100 |     |     |     | 105 |     |     |     |     | 110 |     |
| --- | --- | --- | --- | --- | --- | --- | --- | --- | --- | --- | --- | --- | --- | --- | --- |

Cys Asn Ile Ala Ala Val His Gly Ser Thr His Lys Tyr Met Arg Gly
       115                    120                 125

Thr Leu Leu Ser Leu Val Ser Pro Thr Met Ile Arg Asp His Ile Leu
    130                   135              140

Pro Lys Val Asp Gln Phe Met Arg Ser His Leu Ser Asn Trp Gln Asn
145                 150               155               160

His Val Ile Asp Ile Gln Gln Lys Thr Lys Glu Met Ala Phe Leu Ser
             165               170               175

Ser Leu Lys Gln Ile Ala Gly Ile Glu Ser Ser Thr Ala Gln Leu
    180                   185              190

Phe Met Ser Glu Phe Lys Leu Val Glu Gly Thr Leu Ser Leu Pro
       195               200             205

Ile Asp Leu Pro Gly Thr Asn Tyr Arg Arg Gly Phe Gln Ala Arg Lys
    210                   215              220

Val Ile Val Asn Ile Leu Thr Gln Leu Ile Lys Glu Arg Arg Ala Ser
225                 230               235               240

Lys Thr Lys Asp Val Asp Ile Leu Asn Cys Leu Leu Lys Glu Glu
             245               250               255

Asn Lys Tyr Lys Leu Ser Asp Glu Glu Ile Ile Asp Leu Ile Ile Thr
             260               265               270

Leu Ala Tyr Ser Gly Tyr Glu Thr Val Ser Thr Thr Ser Met Met Ala
       275               280               285

Val Lys Tyr Leu His Asp His Pro His Val Leu Glu Glu Leu Arg Lys
    290                   295              300

Glu His Leu Ala Ile Arg Ala Lys Lys Lys Pro Gly Asp Pro Ile Asn
305                 310               315               320

Trp Glu Asp Tyr Lys Ala Met Lys Phe Thr Arg Ala Val Ile Phe Glu
             325               330               335

Thr Ser Arg Leu Ala Thr Ile Val Asn Gly Val Leu Arg Lys Thr Thr
             340               345               350

Lys Glu Met Glu Ile Asn Gly Phe Val Ile Pro Glu Gly Trp Arg Ile
       355               360               365

Tyr Val Tyr Thr Arg Glu Val Asn Tyr Asp Pro Tyr Leu Tyr Pro Asp
    370                   375              380

Pro Leu Val Phe Asn Pro Trp Arg Trp Leu Asp Arg Ser Leu Glu Ser
385                 390               395               400

Lys Asn Tyr Phe Leu Ile Phe Gly Gly Gly Thr Arg Gln Cys Pro Gly
             405               410               415

Lys Glu Leu Gly Ile Ala Glu Ile Ser Thr Phe Leu His Tyr Phe Val
             420               425               430

Thr Arg Tyr Arg Trp Glu Glu Glu Gly Asn Lys Leu Val Lys Phe
       435               440               445

Pro Arg Val Glu Ala Pro Asn Gly Leu Arg Ile Arg Val Ser Ser Tyr
    450                   455              460

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gctggtattg aatcaagctc                                                  20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggtacttgac agccatcatt                                           20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ttcgcaagac ccttcctcta                                           20

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
ctaataactc gaaactcgaa tgc                                       23

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
tctttttcat cttttcactt ctcc                                      24

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
tgatatagac gttgtggctg ttg                                       23

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
gatgttaccc ccaaaactgc t                                         21

<210> SEQ ID NO 10
<211> LENGTH: 21
<212> TYPE: DNA
<213> ORGANISM: Artificial Sequence
<220> FEATURE:

```
<223> OTHER INFORMATION: primer

<400> SEQUENCE: 10
aacaacatgc tttccatcca g                                                    21
```